United States Patent [19]

Johnson et al.

[11] Patent Number: 4,758,433

[45] Date of Patent: Jul. 19, 1988

[54] **OIL EXTRACT OF *TANACETUM PARTHENIUM* FOR TREATING MIGRAINE**

[75] Inventors: Edward S. Johnson, Maidenhead; Peter J. Hylands; Deborah M. Hylands nee Jessup, both of Wickham, all of England

[73] Assignee: R. P. Scherer Corp., Troy, Mich.

[21] Appl. No.: 749,008

[22] Filed: Jun. 26, 1985

Related U.S. Application Data

[63] Continuation-in-part of Ser. No. 494,964, May 16, 1983, abandoned.

[30] Foreign Application Priority Data

May 19, 1982 [GB] United Kingdom ............... 8214572
Sep. 22, 1982 [GB] United Kingdom ............... 8227062

[51] Int. Cl.$^4$ ............................................ A61K 35/78
[52] U.S. Cl. .................................. 424/195.1; 514/468; 549/299
[58] Field of Search ................... 549/299; 514/468; 424/195.1

[56] References Cited

PUBLICATIONS

El-Feraly et al., Chem. 89: 87138k.
Joshi, Chem. Abst. 86: 72888u.
Edriguez et al., 86: 72889y.
Picman et al., Chem. Abs. 100: 99724g.
Hausen et al., Chem. Abs. 100: 18845 x.
Djermanovic et al., Chem. Abst. 97: 212667a.
Mladenovic et al., Chem. Abst. 97: 212668b.
Bohlmann et al., Chem. Abst. 97: 159479n.
Stevens, Chem. Abst. 97: 159480t.
Hladon et al., Chem. Abst. 91: 68299p.
Ogura et al., Chem. Abst. 90: 23285u.
Lee et al., Cancer Research 31, 1649-1654, Nov. 1971.
Soucek et al., Collective Czech. Chem. Comm., 1961, vol. 26, pp. 803-809.
Blakeman, Chem. Abst. 91: 207614c.
Romo et al., Tetrahedron, 1965, vol. 21, pp. 1744-1745.
Hall et al., Journal of Pharmaceutical Sciences, vol. 68, No. 5, May 1979.

*Primary Examiner*—Jane T. Fan
*Attorney, Agent, or Firm*—Omri M. Behr

[57] ABSTRACT

A preparation for pharmaceutical use, especially in the treatment of migraine, arthritis and bronchial complaints contains a sesquiterpene lactone and is recovered from the plant *Tanacetum parthenium* by extraction using a pharmaceutically acceptable oil.

4 Claims, No Drawings

OIL EXTRACT OF TANACETUM PARTHENIUM FOR TREATING MIGRAINE

This is a continuation-in-part of Ser. No. 494,964 filed 5/16/83 now abandoned.

FIELD OF THE INVENTION

This invention relates to sesquiterpene lactones and sesquiterpene lactone-containing plant extracts and preparations for pharmaceutical use, and particularly to compositions which are useful in the treatment of migraine and various arthritic and bronchial conditions.

BACKGROUND OF THE INVENTION

The incidence of migraine is said to be in the region of 12% of the population. Its precise causes have not been determined but certain elements in its causation are well documented.

Neurohumoral and local hormone (autacoid) factors such as noradrenaline, 5-hydroxytryptamine (serotonin), histamine and prostaglandins are implicated in migraine probably acting at the cerebro-vascular level.

There is much evidence to suggest that a disturbance of blood vessel diameter is involved in the migraine process. Thus reports have demonstrated a constriction of cerebral cortical vessels followed by a dilatation during a migraine attack. The vasoconstriction is believed to be due to the release of amines such as noradrenaline from neurones and 5-hydroxytryptamine from platelets. Histamine is also released from mast cells and plays an important role in the migraine variant known as cluster headache (migrainous neuralgia). Drugs with antinoradrenaline, anti 5-hydroxytryptamine and antihistamine activities are all used to alleviate the symptoms of migraine. Evidence that prostaglandins (PG), such as $PGE_2$, $PGF_{2\alpha}$, $PGI_2$ (prostacyclin) or thromboxane $A_2$ are involved comes from the fact that non-steroidal anti-inflammatory drugs such as aspirin, which act by inhibiting the synthesis of prostaglandins, are highly effective for both the prophylactic and acute treatment of migraine.

As to the causes of arthritic conditions, the suppression of prostaglandin synthesis by non-steroidal anti-inflammatory drugs such as aspirin or indomethacin strongly implicates prostaglandins as inflammatory mediators at least in rheumatoid arthritis. Prostaglandin-like material is present in inflammatory perfusates of experimental animals. The E-prostaglandins in low concentrations are striking potentiators of the pain-producing properties of other agonists such as histamine, 5-hydroxytryptamine and plasmakinins (e.g. bradykinin) as well as other features of the inflammatory response such as increased vascular permeability, erythema, white cell accumulation and platelet aggregation.

Patients with bronchial asthma and chronic bronchitis suffer attacks of wheezing and difficulty in breathing. These are due to bronchial narrowing from spasm of the bronchial smooth muscle or from sticky secretions, or more commonly from a combination of the two. The precise causes of the bronchoconstriction in asthma have not been fully elucidated, but it is believed endogenous neurohumoral and autocoid spasmogens such as acetylcholine, 5-hydroxytryptamine (serotonin), histamine, some prostaglandins and leukotrienes may be involved. Allergic reactions to substances in inhaled dust or those absorbed from food may be manifested by bronchoconstriction or urticaria ("nettle-rash") or circulatory collapse caused by the release of histamine or other endogenous substances.

Drugs with spasmolytic actions such as aminophylline are used to treat bronchospasm. Drugs with antihistamine activity are also used in asthma and for wheezing and other symptoms associated with allergic phenomena such as hay fever.

It has been known for many years that sesquiterpene lactones are present in plants, for example, in the family Compositae (see Yoshio, Mabry and Timmermann, "Sesquiterpene Lactones, Chemistry, NMR and Plant Distribution", University of Tokyo Press 1973).

Of these plant Tanacetum parthenium (formerly called Chrysanthenum parthenium and commonly known as feverfew, featherfoil, flirtwort and Bachelor's Buttons) has been put forward in herbal medicine as a possibly effective treatment for migraine when consumed. No serious medical study of this treatment for migraine has apparently been published, nor has there been any consideration of what ingredient or ingredients of the plant might be involved in this alleged efficacy.

Many years ago, it was reported that the sesquiterpene lactones parthenolide and santamarine may be extracted from feverfew using light petroleum and chloroform respectively (see Sorm et al, Coll. Czech. Chem. Comm., (1961), 26, 803 and Romo et al, Tetrahedron, (1965), 21, 1741 respectively). In those publications, there was no indication of any possible medical use for the sesquiterpene lactones.

Some cytotoxic activity of parthenolide and several other sesquiterpene lactones has also been reported some time ago (Lee et al, Cancer Research, (1971), 31, 1649). There is, however, no suggestion in this article that any sesquiterpene lactone or extract containing it may be useful in the treatment of migraine, arthritis or bronchial complaints.

More recently it has been shown that certain sesquiterpene lactones are potent inhibitors of carrageenan-induced edema and chronic adjuvant-induced arthritis in rodents (see Hall, Starnes, Lee and Waddell, J. Pharm. Sci., (1979), 68,537). This article does not, however, suggest that any sesquiterpene lactone has pharmaceutical activity against any complaint, let along against migraine.

SUMMARY OF THE INVENTION

By repeated selective extraction of feverfew material, and extensive in vitro testing of the extracts for biological activity, in particular spasmolytic activity in smooth muscle tests, we have found surprisingly that, of the very many constituents of the plant, extracts containing certain of the compounds within the range of sesquiterpene lactones present have properties strongly indicative of efficacy in the treatment of migraine. This is particularly surprising because the existence of some such compounds in the plant has been known for many years and yet there has been no disclosure or suggestion anywhere in the literature that they possess any useful activity against migraine. Furthermore, at least some of the reports on the use of feverfew in the treatment of migraine suggest taking an aqueous extract of the plant as "tea". This points away from sesquiterpene lactones being active ingredients since they are unlikely to be extracted from the plant by this method.

The indications are that such compounds are alos likely to be efficacious in the treatment not only of migraine but also of bronchial asthmas and arthritic conditions such as rheumatoid arthritis, osteoarthritis and related arthritides. This could not have been predicted from the completely unrelated cytotoxic activity reported by Lee et al (see above).

We have surprisingly found a plant extract which has biological activity strongly indicative of excellent pharmaceutical use, especially in the treatment of migraine, asthma or arthritic conditios. The extract is a sesquiterpene lactone-containing extract from the plant *Tanacetum parthenium* (hereinafter called "feverfew") recovered therefrom by extraction with an oil, for example, a saturated or unsaturated long chain (e.g. $C_{10-25}$) hydrocarbon or fatty acid, e.g. a commercially available vegetable or animal oil such as cocnut oil, soya bean oil, a fish oil, their derivatives such as polyoxyethylated fatty acids, reconstituted glycerides and esters, e.g. sorbitan esters of the above compounds.

Classes of sesquiterpene lactone which include compounds which we find likely to be effective against one or more of migraine, asthama and arthritic conditions are germacranolides and guaianolides, including pseudoguaianolides, especially those sesquiterpene lactones having an α-methylene substituent in the lactone ring. The extract may contain a plurality of sesquiterpene lactones such as these.

A germacranolide which can be extracted from feverfew using a pharmaceutically acceptable oil is parthenolide of the formula

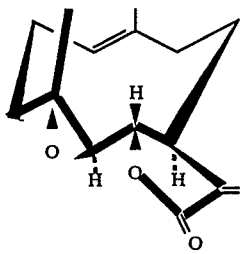

and we find that this compound and extracts from feverfew which contain it are particularly likely to be effective against migraine, asthma and various arthritic conditions.

A sesquiterpene lactone-containing extract in accordance with the invention is regarded as having properties strongly indicative of efficacy in the treatment of migraine, arthritis and asthma if, when subjected to spasmolytic activity tests, the extract shows 100% inhibition of each of at least three agonists, as later described, when the extract contains at least $10^{-4}$ g/ml total sesquiterpene lactone equivalents thereof.

We find that, in general, antagonists which pass this test for spamolytic activity, i.e. inhibition of agonists, are effective in the treatment of migraine, arthritis and asthma. This link between these various complaints does not previously appear to have been disclosed in the literature.

The relationship between spasmolytic activity and the predicted efficacy in the treatment of migraine, arthritis and asthma is as follows:

Although the precise cause or causes of migraine, arthritis and asthma remain unknown, all three are associated with a psotulated local or systemic release of pharmacologically active substances including, in the case of migraine and/or its variants: norepinephrine (noradrenaline), 5-hdorxytryptamine (aerotonin), histamine, prostaglandins and bradykinin; in the case of arthritis: prostaglandins, histamine, 5-hydroxytryptamine and bradykinin; in the case of asthma: histamine, 5-hydroxytryptamine, bradykinin, acetylcholine, prostaglandins and the leukotrienes.

All of these endogenous substances have in common the ability to cause smooth muscle to contract (i.e. go into spasm). Any drug which will act as an antagonist to a wide variety of chemically dissimilar spasmogens is termed a non-selective antagonist or a spasmolytic drug. Many of the above-mentioned chemicals are also pain-producing substances, e.g. 5-hydroxytryptamine, bradykinin, histamine and prostaglandins. Non-selective antagonist drugs will, therefore, not only reduce the smooth muscular spasm (of intracranial blood vessels in the case of migraine, or bronchial smooth muscle in the case of asthma) but also the pain (of migraine and arthritis) associated with their release.

The guinea-pig isolated ileum reacts rapidly and readily to a wide variety of spasmogens and is therefore an ideal preparation on which to screen polyantagonists for potential use in migraine, arthritis and asthma.

The sesquiterpene lactone-containing extract in accordance with the present invention may be obtained from feverfew by mixing the dried, pulverized leaves of the plant with an oil to form a suspension and allowing the mixture to stand to allow extraction of sesquiterpene lactones from the plant.

The suspension may then be stabilised by use of suitable solid fat mixtures, with or without the presence of beeswax or other mineral waxes, colloidal silica, derivatives of cellulose such as carboxy methylcellulose and/or natural gums such as agar or Xanthan, starches, starch derivatives and other suitable carbohydrates, with or without the addition of wetting agents such as sorbitan fatty esters and lecithin.

Where the extract is obtained by forming a stable suspension of dried, pulverized feverfew leaf in the oil, a preparation in accordance with the invention may be formed by encapsulating the suspension in either a hermetically sealed one-piece soft shell or a two-piece hard shell gelatine capsule representing a one unit dose, preferably an approximate amoung of 0.25 to 200 mg, of feverfew leaf with or without the other pharmaceutically active substances.

Alternatively the dried, pulverized feverfew may be allowed to stand in the oil for sufficient time to allow extraction, e.g. 14 days, and then strained to form a macerate or filtered to leave an extract solution.

The suspension, macerate or extract solution may be mixed with surfactive agents or mixtures thereof, such as poleythoxy fatty acid sorbitan esters, mono and di glycerides acetylated glycerides, to form a self-emulsifying system.

A composition in accordance with the invention may be administered as it is, i.e. in the form of a plant extract, but is usually admixed with a pharmaceutically acceptable excipient.

The composition preferably contains from about 0.05 to about 1.5 mg; more preferably about 0.1–1 mg, of active ingredient per gram of composition.

Depending upon the particular crop of feverfew from which the extract is obtained, this concentration of active ingredient may be achieved by suspending in the oil from about 10 to about 200 mg, preferably 15 to 100 mg, of dried feverfew leaves per gram of oil and allowing the oil to extract the active ingredients.

When the composition of the invention is in the form of an encapsulated suspension of dried feverfew leaves in an oil, the amount of feverfew present is preferably from 5 to 75 mg, especially 6 to 50 mg, of feverfew leaves per capsule (capsule capacity about 380 mg). A preferred range of concentrations of active ingredient thus provided is 0.02 to 0.5, especially 0.025 to 0.4 mg per capsule.

A particularly preferred capsule contains about 0.1 mg of active ingredient.

For the treatment of migraine the preparations may be administeed orally or parenterally and conveniently take the form of a tablet, capsule or liquid suspension. They may additionally include, in addition to the sesquiterpene lactones, other known anti-migraine preparations, analgesics and antiemetics as Propranolol Hydrochloride
Ergotamine tartrate
Methysergide Maleate
Dihydroergotamine Mesylate
Clonidine Hydrochloride
Isometheptene Mucate
Buclizine Dihydrochloride
Metoclopramide Hydrochloride
pizotifen Hydrogen Malate
aspirin and other non-steroidal anti-inflammatory agents
paracetamol and other minor analgesics
pentazocine hydrochloride
prochlorperazine
Caffeine
Meprobamate
Ethoheptazine Citrate
Zomepirac
Meptazinol Hydrochloride.

The dosage of active ingredient may be from 0.25 to 200 milligrams per day. In general, from 0.25 to 20 mg per day is sufficient but, in the treatment of an acute attack of migraine or allied disorder the optimal dose range will be higher at about 2 milligrams to 200 milligrams per day.

It is best given in an oral form made up as a tablet, capsule, or as a liquid suspension on a daily basis or regular basis as prescribed by a doctor. One dose should be effective but can be repeated as necessary. However, circumstances may arise where it is best administered by suppository, inhalation or injectio.

For oral administration, the preparation may be admixed with any conventional tabletting or capsuling carrier, or as a suspension in any orally acceptable non-toxic liquid carrier. If desired, the drug may be provided in encapsulated form for sustained release over a period of time. For parenteral administration the drug may be provided as a suspension in any suitable, sterile injection medium, e.g. sterile aqueous saline solution. Given the desired dosage rates indicated above, the appropriate method of formulation of the drug in a form suitable for oral or parenteral administration will be obvious to persons skilled in the art. The same applies for rectal administration, which is also feasible.

Excellent efficacy of a preparation in accordance with this invention is through likely (a) in the treatment of classical and common migraine; (b) in the treatment of migrainous neuralgia (cluster headache); and (c) in the treatment of premenstrual and menstrual migraine and other headaches.

The preparations are likely to be useful in the prevention of the above types of headache, being effective in reducing the frequency, severity and duration of the attacks. They should also be effective in reducing the nausea and vomiting associated with such attacks, or nausea and vomiting as isolated symptoms. They can probably also be used to treat the acute attacks of the above sorts of headache reducing their duration, severity and associated symptoms.

The precise reason for the effectiveness of these preparations in the treatment of migraine is not known but it is hypothesised that in the disorder of migraine and its associated conditions there is an altered reactivity of the cerebral blood vessels to biogenic amines and prostaglandins released locally or into the systemic circulation. Based on this hypothesis, it is believed that the effects of a preparation in accordance with the invention in the treatment of migraine may be the result of a stabilisation of the blood vessel smooth muscle cell membranes leading to a direct inhibition or reduction of their responsiveness to biogenic amines and prostaglandins or to an indirect action by the inhibition of the effects of these substances on the nerves to the intracranial blood vessels.

We find that preparations in accordance with the invention block the actions of neurohumoral transmitters and autocoids such as acetylcholine, noradrenaline, 5-hydroxytryptamine, histamine, bradykinin and prostaglandin $E_2$ on smooth muscle. Furthermore chronic administration of the extracts to guinea-pigs causes a progressive decrease in the reactivity of their smooth msucle to 5-hydroxytryptamine and histamine. Indeed we find that such tests may be carried out on a particular preparation to determine its likely efficacy in the treatment of migraine.

For the treatment of arthritic conditions, preparations in accordance with the invention may be administered orally, rectally, parenterally or by inhalation and conveniently take the form of a tablet, capsule, suppository or liquid suspension.

The dosage of active ingredient may be from 0.25 to 200 mg per day. In general, from 0.25 to 20 mg per day is sufficient but, in the treatment of an acute attack of rheumatoid arthritis or allied disorder the optimal dose range will be higher at about 2 milligrams to 200 milligrams per day.

It is best given in an oral form made up as a tablet or as a liquid suspension on a daily basis or regular basis as prescribed by a doctor. One dose should be effective but can be repeated as necessary. However circumstance may arise where it is best administered by suppository, inhalation or injection.

A preparation in accordance with the invention may additionally include other antiarthritis agents including non-steroidal antiinflammatory drugs, analgesics, skeletal muscle relaxants, steroids, gold and penicillamine.

Examples of such agents are
aspirin,
indomethacin,
piroxicam,
benorylate,
ibuprofen,
paracetamol,
salicylamine,
diflunisal,
ethoheptazine,
fenoprofen(calcium fenoprofate)
flufenamic acid,
mefenamic acid,
naproxen sodium, ketoprofen,
phenylbutazone,
sulindac,
penicillamine,
salsalate,
fenclofenac,
flurbiprofen,
fenbufen,
feprazone,
sodium aurothiomalate,
naproxen,
benoxaprofen,
aloxiprin,
hydroxychloroquine sulphate,
azapropazone,
oxyphenbutazone,
tolemtin,
choline magnesium trisalicylate,
diclofenac,
adrenal steroids such as prednisone or prednisolone.

As to oral administration of the preparation for arthritis treatment, see the remarks above.

Efficacy of a preparation in accordance with this invention is indicated (a) in the treatment of rheumatoid arthritis; (b) in the treatment of osetoarthritis; and (c) in the treatment of arthritis associated with Felty's syndrome, Still's disease, systemic lupus erythematosus, polyarteritis nodosa, scleroderma, gout, achalasia of the cardia, Crohn's disease, chronic brucellosis, ankylosing spondylitis, sarcoidosis, psoriasis and gonorrhoea.

The preparations are likely to be useful in the prevention of the above arthritides, being effective in reducing the frequency, severity and duration of the attacks. The preparations can also be used to treat the acute attacks of the above arthritides reducing their duration, severity and associated symptoms.

The precise reason for the likely effectiveness of these substances in the treatment of arthritis is not known but is is hypotehsised that in rheumatoid arthritis and its associated conditions prostaglandins and other substances such as histamine, 5-hydroxytryptamine and bradykinin are released in and around joints. Prostaglandins potentiate the pain-inducing properties of the other substances. Based on this hypothesis, it is believed that the likely effects of a preparation in accordance with the invention in the treatment of arthritic conditios may be the result of their antiprostaglandin, antihistamine, anti-5-hydroxytryptamine and antibradykinin actions.

We find that preparations in accordance with the invention have marked spasmolytic actions against a wide variety of smooth muscle spasmogens. Thus they block the actions of histamine, 5-hydroxytryptamine, bradykinin and prostaglandin $E_2$. Thus they oppose the pharmacological actions of the most commonly-implicated mediators of chronic inflammation. We find that such tests may be carried out on a particular preparation to determine its likely efficacy in the treatment of rheumatoid arthritis and associated conditions.

For the treatment of asthma, preparations in accordance with the invention may be administered orally, rectally, parenterally or by inhalation.

The dosage of active ingredient may be from 0.25 to 200 milligrams per day. In general, from 0.25 to 20 mg per day is sufficient, but in the treatment of an acute attack of asthma or allied disorder the optimal dose range will be higher at about 2-200 mg per day.

It is best given in an oral form made up as a tablet or capsule or as a liquid suspension on a daily or regular basis as prescribed by a doctor. One dose may be effective but can be repeated as necessary. However, circumstances may arise where it is best administered by suppository, inhalation or injection.

In addition to the sesquiterpene lactone, the preparation may also contain other ingredients such as bronchodilator, antihistamine and anti-infective agents, examples of which agents are
isoprenaline sulphate,
orciprenaline,
adrenaline,
terbutaline sulphate,
theophylline,
choline theophyllinate,
aminophylline,
ephedrine hydrochloride,
papaverine hydrochloride,
ipratropium bromide,
atropine methonitrate,
beclomethasone dipropionate,
fenoterol hydrobromide,
betamethasone,
isoetharine mesylate or hydrochloride,
phenylephrine hydrochloride or bitartrate,
thenyldiamine hydrochloride,
reproterol hydrochloride,
deptropine citrate,
butethamate citrate,
acepifylline,
dipheylpyraline hydrochloride,
sodium cromoglycate,
etamiphylline camsylate,
theophylline monoethanolamine,
etafedrine hydrochloride,
bufylline,
guaiphenesin,
diphenydramine hydrochloride and other histamine $H_1$-receptor antagonists,
diprophylline,
methoxyphenamine hydrochloride,
rimiterol hydrobromide,
hyoscine hydrobromide,
salbutamol sulphate,
ketotifen hydrogen fumarate,
pseudo-ephedrine hydrochloride,
bromhexine hydrochloride, and
antifungal, antibacterial and antiviral agents.

As to oral administration for treatment of asthma, see the remarks above.

Efficacy of a preparation in accordance with this invention is indicated (a) in the treatment of bronchial asthma; (b) in the treatment of bronchoconstriction associated with chronic bronchitis; (c) in the treatment of symptoms associated with histamine release in allergic hypersensitivity phenomena such as hay fever and anaphylaxis.

The preparations can also be co-administered with other bronchodilator, antihistamine and anti-infective agents as enumerated above.

The precise reason for the proposed effectiveness of these substances in the treatment of asthma and other allergic reactions, rests on their ability to prevent or inhibit smooth muscle spasm caused by a variety of endogenous substances such as acetylchloine, histamine, 5-hydroxytryptamine, bradykinin and prostaglandins capable of being released locally or into the systemic circulation. Thus the excellent effects of a preparation in accordance with the invention in the treatment of bronchoconstriction may be the result of a stabilisation of the smooth muscle cell membranes leading to a direct inhibition or reduction of their responsiveness to biogenic amines, prostaglandins and polypeptides, or to an indirect action by the inhibition of the effects of these substances on the nerves to the bronchial musculature and/or mucus secreting cells.

We find that preparations in accordance with the invention block the spasms (contractions) of smooth muscle caused by acetylcholine, 5-hydroxytryptamine, histamine, prostaglandin $E_2$ and bradykinin. Indeed we find that such spamolytic activity tests can be carried out on a particular preparation to determine its likely efficacy in the treatment of bronchial complaints.

DETAILED EXPLANATION OF PREFERRED EMBODIMENTS

Spasmolytically active compositions in accordance with the invention and the efficacy of such preparations will now be illustrated in more detail with reference to the following Examples.

Preparation of Capsules

EXAMPLE 1

Powdered feverfew leaf and soya bean oil are mixed in the following proportions:

| Powdered feverfew leaf | 10.0 kg |
| Soya Bean Oil | 100.0 kg |

The mixture is allowed to stand for 14 days with stirring for extraction of the active ingredients and then stabilized by:

| Lecithin | 2.2 kg |
| Hydrogenated Fats | 30.0 kg |
| Beeswax | 10.0 kg |

The mixture is encapsulated into a soft shell capsule or hard shell capsule, representing a dose of 25 mg of dried leaf. This fills into a 7.5 oval soft shell capsule or a number 2 hard shell capsule with a target fill weight of 380.5 mg.

In an alternative method, the mixture is strained and the resulting macerate, encapsulated as the oily extract, is stabilised with one or more of the above described suspending agents, into soft shell or two piece hard shell gelatin capsules.

EXAMPLE 2

Powdered feverfew leaf and cod liver oil are mixed in the following proportions:

| Feverfew Dry Leaf | 10.0 kg |
| Cod Liver Oil | 100.0 kg |

The mixture is allowed to stand for 14 days for extraction of the active ingredients.

The resultant mixture is filtered and the filtrate encapsulated at a fill weight of 250 mg per unit dose, to represent approximately 25 mg of dried leaf in a soft shell or two piece hard shell capsule.

In an alternative method the suspension or macerate is mixed with surfactive agents or mixtures thereof, such as polyethoxy fatty acid sorbitan esters, mono and di glycerides or acetylated glycerides, to form a self emulsifying system.

The resultant formulation is encapsulated into a soft shell or two piece hard shell capsule.

It is predicted that mixtures and dosages will enhance absorption of the oily active principles via the lymphatic system.

EXAMPLE 3

The following are mixed:

| Feverfew dry leaf macerate (as above) | 100.0 kg |
| Polyethoxy sorbitan monooleate | 37.0 kg |
| Mono and di glycerides blend | 29.0 kg |

These are mixed and encapsulated at a dosage fill weight of 415 mg into soft shell or two piece hard shell capsule, representing approximately 25 mg of dried feverfew leaf.

The soft shell or two piece hard shell gelatin capsule may be used via the oral or rectal route.

They may be treated to retard disintegration or absorption by the use of gastro resistant coatings, such as hydroxymethyl propyl cellulose or the content may be mixed with polymeric matrix materials as known to the pharmaceutical industry, to release the active principles at a controlled rate.

SPASMOLYTIC ACTIVITY TESTS

In order to demonstrate the spasmolytic activity of a composition in accordance with the invention, the stabilized mixture formed in Example 1 was filtered to remove remaining feverfew leaves and the resultant sesquiterpene-lactone containing extract was subjected to spasmolytic activity tests as follows. Appropriate amounts of the extract were tested for spasmolytic activity using acetylcholine (ach), 5-hydroxytryptamine (5-HT), histamine and prostaglandin $E_2$ as agonists as described below.

Guinea pigs weighing 200–300 g were killed by a blow on the head. The proximal ileum was excised and 2–3 cm lengths were cleaned and suspended in Krebs solution (NaCl 118.4, KCl 4.7, $CaCl_2$ 2.5, $MgSo_4$ 1.2, $Kh_2PO_4$ 1.2, $HaHCO_3$ 25 and glucose 11.5 mMole/liter) at 37° C. through which a mixture of 95% $O_2$ and 5% $CO_2$ was constantly bubbled. The lengths of ileum were set up to record longitudinal contractions isometrically. Log (dose) vs response curves were recorded to acetylcholine, 5-hydroxytryptamine, histamine and prostaglandin $E_2$ from which $ED_{50}$ doses were taken and given repeatedly until constant responses were achieved. The antagonist i.e. the oil extract, was then dissolved in the minimum of dimethylsulphoxide and made up to a concentration of $10^{-4}$ g/ml with Krebs solution. This was added to the bath containing the ileum and left for 30 minutes. After thorough washing with Krebs solution to remove the residual antagonist the responses of the tissue to be agonists were then recorded and the percentage change calculated.

A control experiment was performed in exactly the same way except the antagonist was omitted. (This was essential since leaving un undosed tissue for 30 minutes often increases its sensitivity to exogenous agonist).

The sesquiterpene lactone-containing oil extract showed 100% inhibition to the four agonists, whereas an oil containing no active ingredient did not show such inhibition.

Chromatographical analysis of the oil extracts showed that the different oils each gave an extract of a different respective chemical constitution, with differing sesquiterpene lactones and amounts thereof. However in each of the extracts so analysed, the major sesquiterpene lactone constituent was parthenolide.

We claim:

1. A method of alleviating migraine in a human being which method comprises administering to the human being, a spasomolytically active composition comprising a solution of a spasmolitically effective amount of an extract of the plant *Tanacetum parthemium* in a pharmacuetically acceptable oil, comprising at least one sesquiterpene lactone and which solution is obtained by extraction of the dried said plant with the said pharmaceutically acceptable oil, the oil being selected from the group consisting of saturated and un-saturated long chain hydrocarbons and fatty acids, vegetable and animal oils and ployoxeyethylated derivatives thereof and reconstituted glycerides and esters thereof, wherein said hydrocarbon chain comprises between 10 and 25 carbon atoms.

2. A method according to claim 1, wherein the oil is selected from the group consisting of coconut oil soybean oil and fish oil.

3. A method according to claim 1, which comprises administering to the human being an effective amount of an encapsulated preparation comprising the said spasomolytically active composition.

4. A method according to claim 1, wherein the extract contains parthenolide.

* * * * *